(12) United States Patent
Mangiardi

(10) Patent No.: US 9,149,565 B2
(45) Date of Patent: Oct. 6, 2015

(54) BIODEGRADABLE SUPPORTING DEVICE

(71) Applicant: Q3 MEDICAL DEVICES LIMITED, Dublin (IE)

(72) Inventor: Eric K. Mangiardi, Charlotte, NC (US)

(73) Assignee: Q3 MEDICAL DEVICES LIMITED, Dublin (IE)

( * ) Notice: Subject to any disclaimer, the term of this patent is extended or adjusted under 35 U.S.C. 154(b) by 0 days.

(21) Appl. No.: 14/174,600

(22) Filed: Feb. 6, 2014

(65) Prior Publication Data

US 2014/0147575 A1 May 29, 2014

Related U.S. Application Data

(63) Continuation of application No. 13/416,074, filed on Mar. 9, 2012, now Pat. No. 8,834,902.

(51) Int. Cl.
| | |
|---|---|
| *A61L 31/10* | (2006.01) |
| *A61K 9/00* | (2006.01) |
| *A61K 35/12* | (2015.01) |
| *A61K 31/436* | (2006.01) |
| *A61P 9/04* | (2006.01) |
| *A61L 31/02* | (2006.01) |
| *A61K 31/337* | (2006.01) |
| *A61F 2/86* | (2013.01) |
| *A61L 31/00* | (2006.01) |
| *A61L 31/14* | (2006.01) |
| *A61L 31/16* | (2006.01) |
| *A61B 17/12* | (2006.01) |
| *A61F 2/07* | (2013.01) |
| *A61F 2/82* | (2013.01) |
| *B82Y 5/00* | (2011.01) |

(52) U.S. Cl.
CPC ......... *A61L 31/022* (2013.01); *A61B 17/12113* (2013.01); *A61F 2/07* (2013.01); *A61F 2/82* (2013.01); *A61F 2/86* (2013.01); *A61K 31/337* (2013.01); *A61K 31/436* (2013.01); *A61L 31/005* (2013.01); *A61L 31/10* (2013.01); *A61L 31/14* (2013.01); *A61L 31/148* (2013.01); *A61L 31/16* (2013.01); *A61F 2250/003* (2013.01); *A61L 2300/416* (2013.01); *A61L 2300/64* (2013.01); *A61L 2420/08* (2013.01); *B82Y 5/00* (2013.01)

(58) Field of Classification Search
CPC ....... A61F 2250/003; A61F 2/07; A61F 2/82; A61F 2/86; A61L 2420/08; A61L 31/14; A61L 31/148
See application file for complete search history.

(56) References Cited

U.S. PATENT DOCUMENTS

| | | | |
|---|---|---|---|
| 4,642,104 A | | 2/1987 | Sakamoto et al. |
| 5,653,745 A | | 8/1997 | Trescony et al. |
| 6,569,195 B2 | | 5/2003 | Yang et al. |
| 2003/0040754 A1 | | 2/2003 | Mitchell et al. |
| 2004/0030377 A1 | | 2/2004 | Dubson et al. |
| 2006/0229711 A1 * | 10/2006 | Yan et al. .................... 623/1.38 |
| 2007/0043433 A1 * | 2/2007 | Chandrasekaran .......... 623/1.46 |
| 2007/0135908 A1 * | 6/2007 | Zhao ............................ 623/1.46 |
| 2007/0270939 A1 | | 11/2007 | Hood et al. |
| 2008/0319536 A1 | | 12/2008 | Houston et al. |
| 2010/0034960 A1 * | 2/2010 | Kindaichi et al. ........... 427/2.25 |
| 2010/0076544 A1 | | 3/2010 | Hoffmann et al. |
| 2010/0076556 A1 * | 3/2010 | Tomantschger et al. ... 623/11.11 |
| 2011/0307053 A1 | | 12/2011 | Gale et al. |

OTHER PUBLICATIONS

European Search Report issued in European Application 09842845.1 dated Nov. 19, 2014.
Pending U.S. Appl. No. 13/416,074, filed Mar. 9, 2012.
International Search Report and Written Opinion issued in International Patent Application No. PCT/US2012/028448 mailed Nov. 23, 2012.
McGovren, "Chapter 2: Pharmacologic Principles," Cancer Chemotherapy Handbook, 2nd Edition, 1994, pp. 15-34.
File history of U.S. Appl. No. 13/416,074, filed Mar. 9, 2012.

* cited by examiner

*Primary Examiner* — Anna Falkowitz
(74) *Attorney, Agent, or Firm* — Ping Wang; Andrews Kurth LLP

(57) ABSTRACT

A biodegradable in vivo supporting device is disclosed. The in vivo supporting device comprises a biodegradable metal scaffold and a biodegradable polymer coating covering at least a portion of the biodegradable metal scaffold, wherein the biodegradable polymer coating has a degradation rate that is faster than the degradation rate of the biodegradable metal scaffold.

16 Claims, 4 Drawing Sheets

US 9,149,565 B2

BIODEGRADABLE SUPPORTING DEVICE

This application is a continuation application of U.S. patent application Ser. No. 13/416,074, filed on Mar. 9, 2012. The entirety of the aforementioned application is incorporated herein by reference.

FIELD

The present application generally relates to medical devices and, in particular, to a biodegradable in vivo supporting device.

BACKGROUND

In vivo supporting devices or barrier devices, such as stents, is a man-made "tube" or "frame" inserted into a natural passage or conduit in the body to prevent, or counteract, a disease-induced, localized flow constriction or flow outflow like a leak or aneurysm. Supporting devices include vascular supporting devices, non-vascular supporting devices, and heart failure closure or aneurysm sealing devices. Vascular supporting devices are designed for applications in the vascular system, such as arteries and veins. Non-vascular supporting devices are used in other body lumens such as biliary, colorectal, esophageal, ureteral and urethral tract, and upper airway. Heart failure closure devices are used to correct defects in heart, such as atrial septal defect (ASD), patent foramen ovale (PFO) and ventricular septal defect (VSD). Aneurysm sealing devices are used to close off potentially dangerous aneurysm or pseudo aneurysm throughout the vascular and non-vascular system.

In vivo supporting devices are typically made from a rigid material, such as a metal, alloy or rigid polymeric material. The supporting device may be made from a biodegradable material so that there is no need to remove the device after the correction of the underline defects. A common problem with the biodegradable supporting device, however, is that the device may disintegrate in an uncontrolled manner and break into large pieces which, if entering the circulation of a body fluid such as blood, may interfere with the normal circulation of the body fluid. Therefore, there exists a need for improved in vivo supporting devices that are biodegradable in a controlled manner.

SUMMARY

One aspect of the present invention relates to an in vivo supporting device. The device comprises a biodegradable metal scaffold and a biodegradable polymer coating that coats at least a portion of the biodegradable metal scaffold. In certain embodiments, the biodegradable polymer coating has a degradation rate that is faster than the degradation rate of the biodegradable metal scaffold. In other embodiments, the biodegradable polymer coating has a degradation rate that equals to, or is slower than, the degradation rate of the biodegradable metal scaffold.

In other embodiments, the biodegradable metal scaffold comprises an alloy comprising magnesium.

In other embodiments, the biodegradable metal scaffold is made from a magnesium alloy having a magnesium content of at least 96 wt. %, a manganese content of at least 1 wt. %, and at least one metal from the rare earth metal group in the amount of at least 0.5 wt. %.

In other embodiments, the biodegradable metal scaffold is made from a magnesium alloy having a magnesium content of 96-97.9 wt. %, a manganese content of 1.6-2 wt. %, and at least one metal from the rare earth metal group in the amount of 0.5-2 wt. %.

In other embodiments, the biodegradable metal scaffold is made from a magnesium alloy having a magnesium content of 97.45 wt. %, a manganese content of 1.8 wt. %, and a cerium content of 0.75 wt. %.

In some embodiments, the biodegradable polymer coating coats metal struts of the biodegradable metal scaffold but does not cover openings between struts. In other embodiments, the biodegradable polymer coating coats metal struts of the biodegradable metal scaffold and covers openings between struts. In yet other embodiments, the in vivo supporting device comprises a biodegradable polymer coating that coats metal struts of the biodegradable metal scaffold but does not cover openings between struts, and a biodegradable polymer covering that covers the coated metal struts and openings between the metal struts.

In related embodiments, the biodegradable polymer coating or covering contains a drug that is distributed uniformly throughout the coating or covering. In another related embodiment, the drug is distributed non-uniformly throughout the coating or covering.

In other embodiments, the biodegradable polymer coating or covering has a uniform thickness of 10 μm-200 μm (i.e., the coating/covering has the same thickness throughout the coated/covered area). In other embodiments, the biodegradable polymer coating or covering has a thickness that varies within the range of 10 μm-200 μm (i.e., the coating/covering has different thickness in different areas).

In other embodiments, the biodegradable metal scaffold comprises metal struts, wherein the metal struts are covered by a biodegradable polymer coating having one or more holes that allow direct contact of the metal strut with a body fluid when the supporting device is placed inside a body lumen.

In other embodiments, the biodegradable metal scaffold comprises metal struts, wherein the metal struts are partially covered by the biodegradable polymer coating.

In other embodiments, the biodegradable metal scaffold comprises metal, wherein the metal struts are covered on surfaces that would otherwise be exposed to a body lumen.

In other embodiments, the in vivo supporting device is a closure device such as heart failure closure devices for atrial septal defect (ASD), patent foramen ovale (PFO) and ventricular septal defect (VSD), and closure devices for fistula and aneurysm, and the biodegradable polymer coating covers the entire exterior surface of the biodegradable metal scaffold, including spaces between metal struts of the metal scaffold. In other embodiments, the a biodegradable polymer covering that covers the entire exterior surface of the biodegradable metal scaffold, including spaces between the metal struts.

In another embodiment, the biodegradable polymer coating is a multi-layer coating comprising an outer layer having a first degradation rate and an inner layer having a second degradation rate. In certain embodiments, the first degradation rate is faster than the second degradation rate. In other embodiments, the first degradation rate equals to, or is slower than, the second degradation rate.

In a related embodiment, the outer layer comprises an agent, such as paclitaxel, and sirolimus, that prevents or reduces the post-implantation hyperplastic response or healing. In another related embodiment, the outer layer comprises stem cells.

In another related embodiment, the inner layer comprises an agent, such as paclitaxel and sirolimus, that prevents or reduces the post-implantation hyperplastic response. In another related embodiment, the inner layer comprises stem cells.

In another embodiment, the biodegradable metal scaffold constitutes less than 50% w/w of the in vivo supporting device.

In another embodiment, the biodegradable metal scaffold constitutes less than 50% w/v of the in vivo supporting device.

In another embodiment, the biodegradable metal scaffold constitutes less than 50% v/v of the in vivo supporting device.

In another embodiment, the biodegradable metal scaffold contributes less than 50% of the structure performance of the in vivo supporting device.

In another embodiment, the in vivo supporting device comprises magnesium as a minor component.

In another embodiment, the biodegradable metal scaffold has a magnesium content that is less than 50% w/w of the in vivo supporting device.

In another embodiment, the biodegradable metal scaffold has a magnesium content that is less than 50% w/v of the in vivo supporting device.

In another embodiment, the biodegradable metal scaffold has a magnesium content that is less than 50% v/v of the in vivo supporting device.

In another embodiment, the magnesium in the in vivo supporting device contributes to less than 50% of the structure performance of the in vivo supporting device.

In another embodiment, the magnesium is a minor constituent of the biodegradable metal scaffold.

In another embodiment, the biodegradable polymer coating and/or covering comprises a biodegradable polymer and metal particles.

In a related embodiment, the metal particles are selected from particles of iron, magnesium, tantalum, zinc and alloys thereof.

In another related embodiment, the metal particles are nanoparticles of iron, magnesium, tantalum, zinc and alloys thereof.

In another embodiment, the biodegradable metal scaffold is an expandable scaffold that expands after implantation and wherein the biodegradable polymer coating and/or covering is an elastic coating/covering that expands with the biodegradable metal scaffold.

In another embodiment, the biodegradable metal scaffold is an expandable scaffold that expands after implantation and wherein said biodegradable polymer coating and/or covering is a coating/covering that forms fissures when said biodegradable metal scaffold is expands in vivo.

In another embodiment, the biodegradable polymer coating is permeable to body fluid.

Another aspect of the present invention relates to a method for producing a biodegradable in vivo supporting device. The method comprises the steps of (a) producing a biodegradable metal scaffold; (b) coating the biodegradable metal scaffold with a first biodegradable polymer coating having a first degradable rate; and (c) coating the biodegradable metal scaffold from step (b) with a second biodegradable polymer coating having a second degradable rate. In certain embodiments, the second degradable rate is faster than the first degradable rate. In other embodiments, the second degradable rate is slower than the first degradable rate.

In some embodiments, the second biodegradable polymer coating comprises an agent that prevents or reduces the post-implantation hyperplastic response.

In some embodiments, the first and second biodegradable polymer coating covers only the surface of the struts of the metal scaffold but not the openings between the struts. In other embodiments, the first and second biodegradable polymer coating covers the surface of the struts of the metal scaffold and the openings between the struts. In other embodiments, the first and second biodegradable polymer coating covers only the surface of the struts of the metal scaffold but not the openings between the struts, and the coated scaffold is further covered with a covering that covers the openings between the coated struts.

In other embodiments, the first and/or second biodegradable polymer coating comprises a biodegradable polymer and metal particles. In a related embodiment, the metal particles are selected from particles of iron, magnesium, tantalum, zinc and alloys thereof.

In another related embodiment, the metal particles are nanoparticles of iron, magnesium, tantalum, zinc and alloys thereof.

In other embodiments, the first and/or the second coating comprises an agent, such as paclitaxel and sirolimus, that prevents or reduces the post-implantation hyperplastic response or healing. In another embodiment, the first and/or the second coating comprises stem cells.

In other embodiments, the drug is embedded into the first or the second biodegradable polymer coating that covers evenly throughout the biodegradable metal scaffold including openings between struts of the metal scaffold.

BRIEF DESCRIPTION OF DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 4A shows a partially covered stent strut with exposed middle section. FIG. 4B shows a partially covered stent strut with exposed end section. FIG. 4C shows a stent strut with multiple exposed sections.

FIGS. 5A and 5B show a perspective view and a cross-sectional view, respectively, of a stent strut covered with a biodegradable layer on the outer surface. FIGS. 5C-5F show a perspective view and cross-sectional views of another stent strut partially covered with a biodegradable layer.

DETAILED DESCRIPTION

Figure 1:
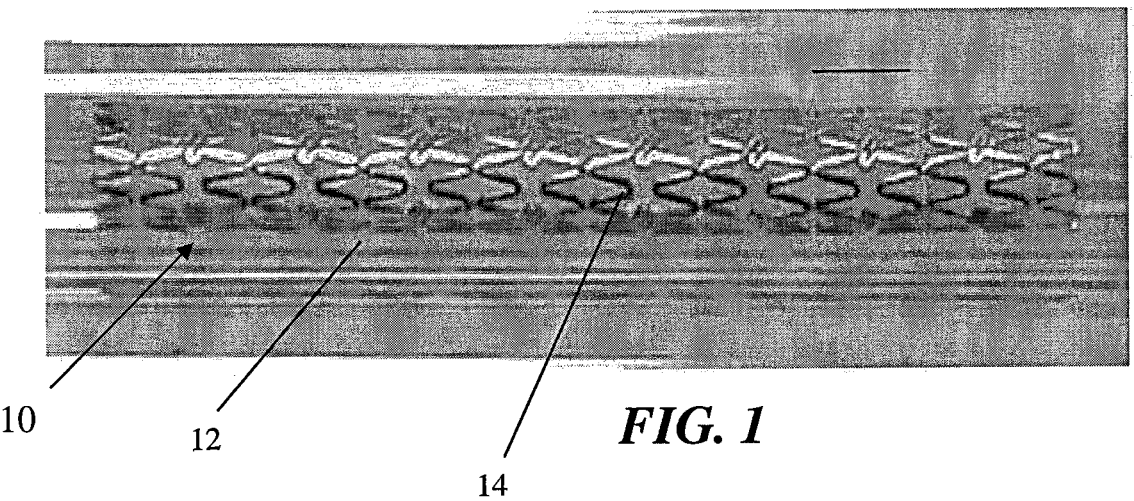
FIG. 1 shows an embodiment of a stent with very thin struts.

The practice of the present invention will employ, unless otherwise indicated, conventional medical devices and methods within the skill of the art. Such techniques are explained fully in the literature. All publications, patents and patent applications cited herein, whether supra or infra, are hereby incorporated by reference in their entirety.

One aspect of the present invention relates to a biodegradable in vivo supporting device. The device contains body formed with a biodegradable metal scaffold coated with a biodegradable polymer coating. Once placed inside a body lumen, the polymer coating is capable of covering the biodegradable metal scaffold long enough for the device to be encapsulated in the surrounding tissue so that fragments of the biodegradable metal scaffold would be degraded and absorbed in situ at the treatment site.

The biodegradable in vivo supporting devices include, but are not limited to, vascular supporting devices such as vascular stents, non-vascular supporting device such as non-vascular stents, and closure/sealing/barrier devices such as devices used to correct defects in heart and devices used to seal fistula and aneurysms.

In some embodiments, the biodegradable polymer coating coats metal struts of the biodegradable metal scaffold but does not cover openings between struts. In other embodiments, the biodegradable polymer coating coats metal struts of the biodegradable metal scaffold and covers openings between struts. In yet other embodiments, the in vivo supporting device comprises a the biodegradable polymer coating that coats metal struts of the biodegradable metal scaffold but does not cover openings between struts, and a biodegradable polymer covering that covers the coated metal struts and openings between the metal struts.

In other embodiments, the biodegradable polymer coating or covering has a uniform thickness of 10 µm-200 µm (i.e., the coating/covering has the same thickness throughout the coated/covered area). In other embodiments, the biodegradable polymer coating or covering has a thickness that varies within the range of 10 µm-200 µm (i.e., the coating/covering has different thickness in different areas).

In some embodiments, the biodegradable polymer coating or covering contains a drug that is distributed uniformly throughout the coating or covering. In another related embodiment, the drug is distributed non-uniformly throughout the coating or covering.

As used herein, the term "biodegradable material" or "bioresorbable material" refers to a material that can be broken down by either chemical or physical process, upon interaction with the physiological environment at the implantation site, and erodes or dissolves within a period of time, typically within days, weeks or months. A biodegradable or bioresorbable material serves a temporary function in the body, such as supporting a lumen or drug delivery, and is then degraded or broken into components that are metabolizable or excretable.

As used herein, the term "metal" refers to both single element metals and alloys.

As used herein, the term "stent" refers to a device which is implanted within a bodily lumen to hold open the lumen or to reinforce a small segment of the lumen. Stents can be used for treating obstructed vessels, biliary ducts, pancreatic ducts, ureters, or other obstructed lumens, fractured canals, bones with hollow centers and/or for delivering various drugs through controlled release to the particular lumen of interest.

As used herein, the diameter of an in vivo supporting device refers to the width across the shaft of the device body. In one embodiment, the device has a uniform diameter along the length of its body. In another embodiment, the device has a variable diameter along the length of its body. In one embodiment, the device has a tubular body with a distal end, a proximal end and a middle section, wherein the diameter at the distal end is smaller than the diameter at the proximal end. In another embodiment, the diameter at the proximal end is smaller than the diameter at the distal end. In yet another embodiment, the diameters at the distal end and the proximate end are both smaller than the diameter at the middle section of the device. In another embodiment, the device is a stent with an elongated tubular body having a distal end, a proximal end and a middle section, and at least one channel formed on or in said body to provide fluid communication between said proximal end and said distal end.

FIG. 1 shows an embodiment of a biodegradable metal scaffold comprising thin struts. In this embodiment, the scaffold 10 comprises a tubular body 12 and thin struts 14. In certain embodiments, the struts 14 has a thickness in the range of 10 µm to 100 ptm.

Figure 2A:
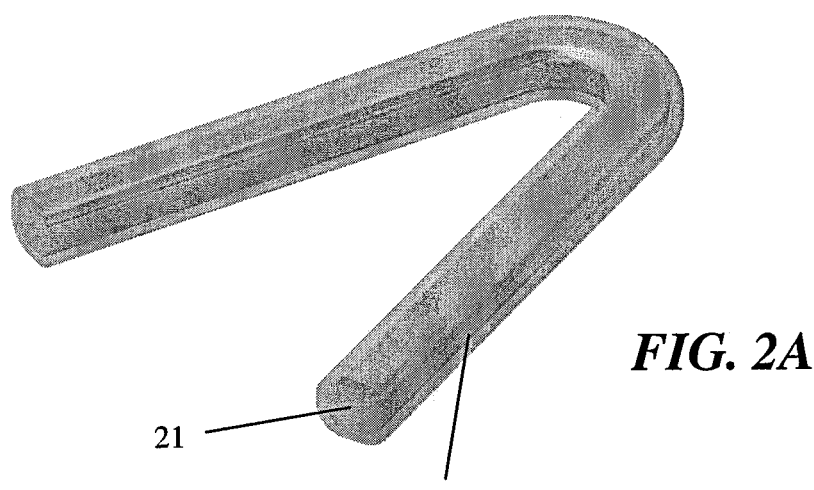
FIGS. 2A-2B show the perspective view (FIG. 2A) and cross sectional view (FIG. 2B) of a stent strut fully covered with a biodegradable polymer coating.
Figure 2B:

In some embodiments, the struts 14 are fully covered with a biodegradable polymer coating layer. FIGS. 2A-2B show the perspective view (FIG. 2A) and cross sectional view (FIG. 2B) of a strut 14 having a metal core 21 fully covered with a biodegradable polymer coating 23. This coating is different from the coating used in perforation management devices. The coating 23 can be of varying thickness. The metal core 21 starts to degrade after the complete degradation of the coating 23.

Figure 3A:
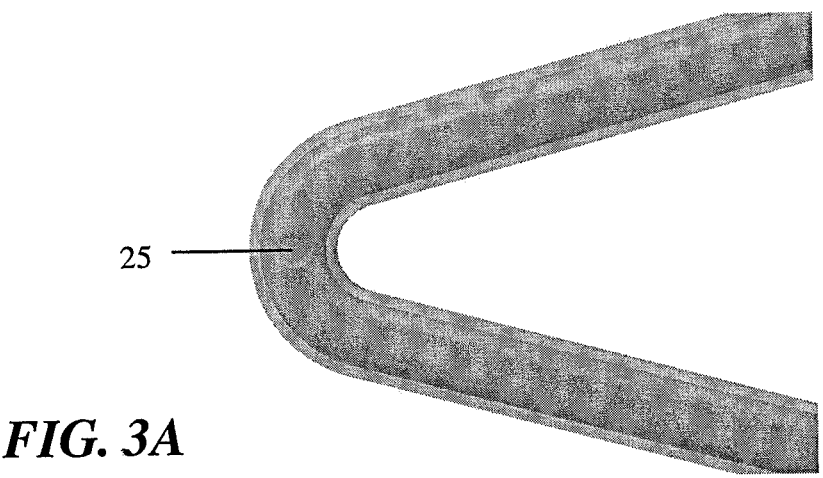
FIGS. 3A-3B show the perspective top view (3A) and cross sectional view (3B) views of a stent strut with a biodegradable core covered with a biodegradable layer and a small opening on the cover.
Figure 3B:
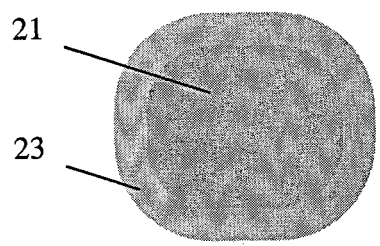

In certain embodiments, the biodegradable polymer coating 23 is a porous coating so as to allow degradation of the inner core 21 before the complete degradation of the coating 23. In some other embodiments, the biodegradable polymer coating layer 23 has one or more small holes in the coating so as to allow degradation of the inner core 21 before the complete degradation of the coating 23. FIGS. 3A-3B show the perspective top view (3A) and cross sectional view (3B) views of a stent strut 14 with a biodegradable core 21 covered with a biodegradable polymer coating 23 and a small opening 25 on the coating 23. The opening 25 allows for direct contact of the inner core 21 with the body fluid and earlier degradation of the core 21.

Figure 4A:
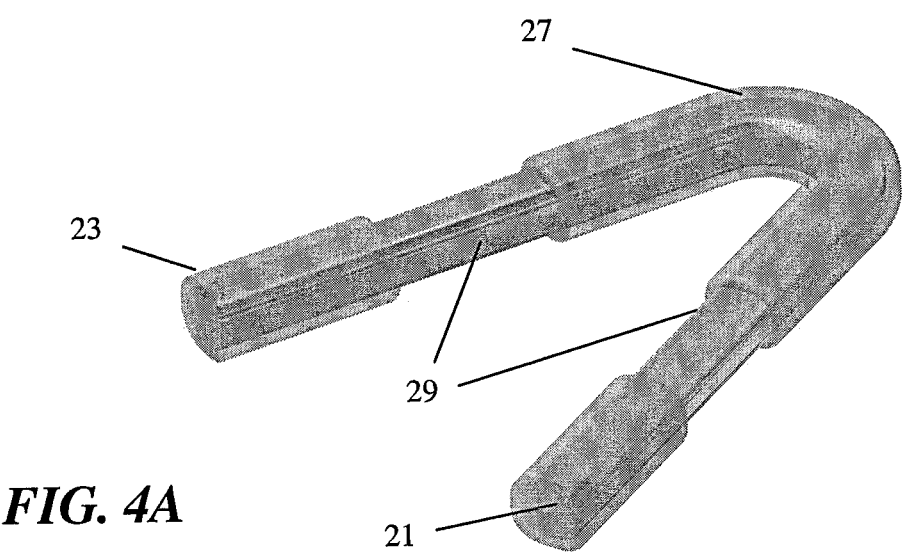
FIGS. 4A-4C show embodiments of stent struts partially covered with a biodegradable layer.
Figure 4B:
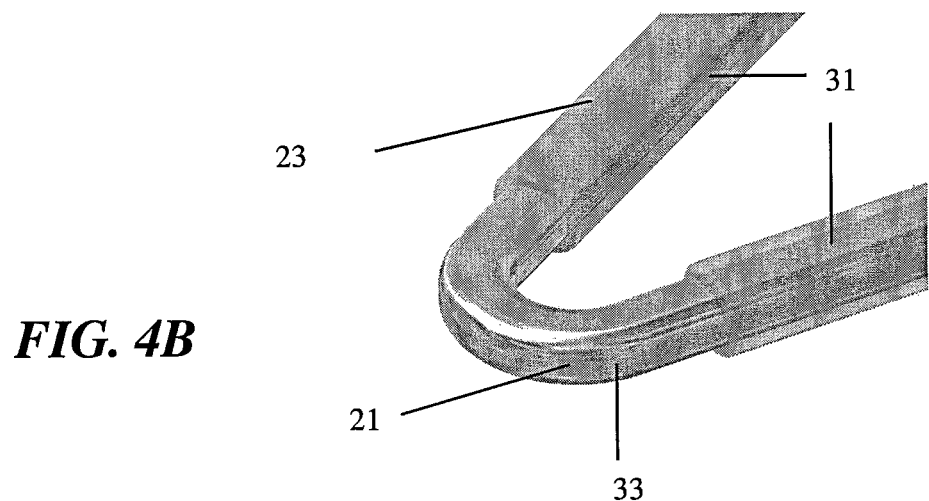
Figure 4C:
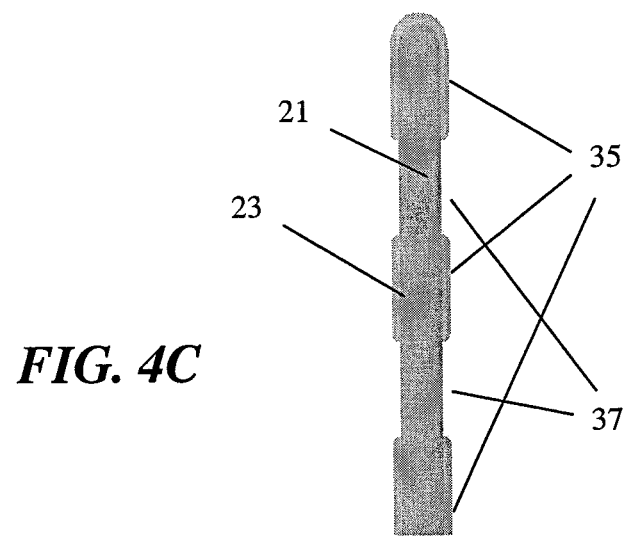

In some other embodiment, the strut 14 comprises a metal core 21 partially covered with a biodegradable polymer coating 23. FIGS. 4A-4C show embodiments of a strut 14 having a metal core 21 with one or more covered sections and one or more exposed sections. In one embodiment, the metal core 21 has covered section 27, and an exposed middle section 29 (FIG. 4A). In another embodiment, the metal core 21 has covered sections 31 and an exposed end section 33 (FIG. 4B). In another embodiment, the metal core 21 has multiple covered sections 35 and multiple exposed sections 37 (FIG. 4C) that allow earlier degradation of the device.

Figure 5A:
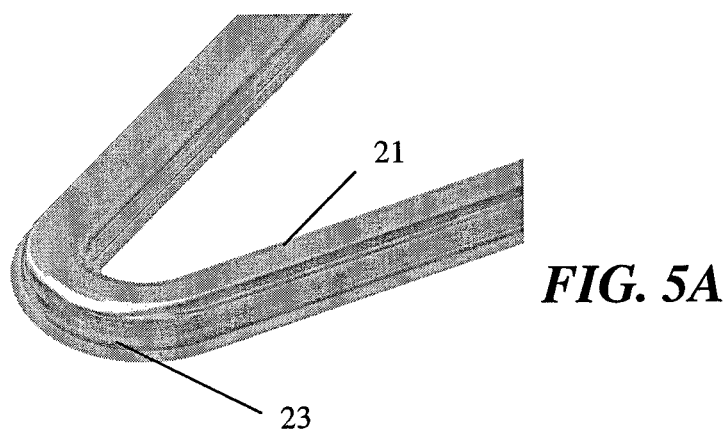
FIGS. 5A-5F show embodiments of stent strut partially covered with a biodegradable layer.
Figure 5B:
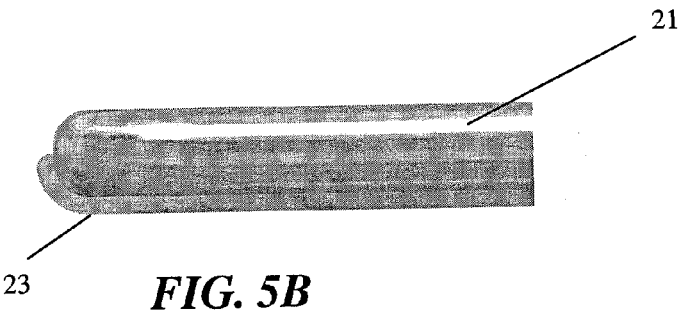
Figure 5C:
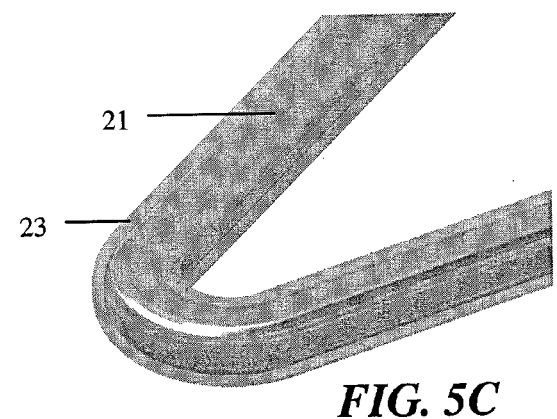
Figure 5D:
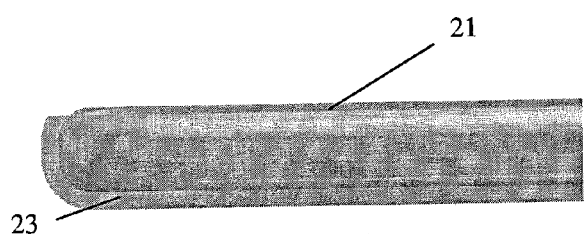
Figure 5F:
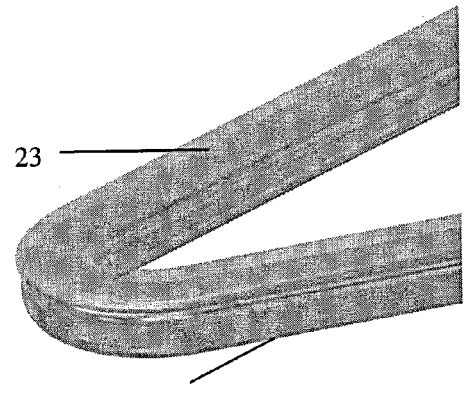
Figure 5E:
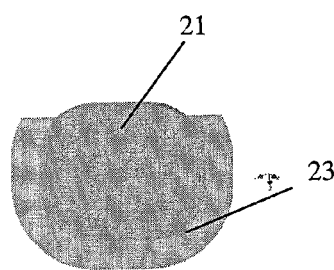

In some other embodiments, the metal core 21 is covered with the biodegradable polymer coating 23 on certain sides and surfaces. In one embodiment, the metal core 21 is covered with the biodegradable polymer coating 23 in such a manner that, when placed in a body lumen, the metal core surfaces that face the lumen opening and are exposed to the body fluid in the lumen are covered with the biodegradable polymer coating 23 to reduce the rate of degradation, while the metal core surfaces that are in contact with the lumen wall are not covered. FIGS. 5A-5E show various embodiments of struts 14 with side-coated metal core 21. FIGS. 5A and 5B show the perspective view (FIG. 5A) and cross sectional view (FIG. 5B) of struts with coatings that cover about half of the strut outer surface. FIGS. 5C-5D show the perspective view (FIG. 5C) and cross sectional views (FIGS. 5D and 5E) of a strut with a coating 23 that cover more than half of the outer surface of the core 14. FIG. 5F, on the other hand, shows the perspective view of struts 14 with coatings that cover less than half of the strut outer surface.

The Biodegradable Metal Scaffold

The metal scaffold or can be made from any biodegradable metal or alloys. Examples of such materials include, but are not limited to, lithium, sodium, magnesium, aluminum, potassium, calcium, cerium, scandium, titanium, vanadium, chromium, manganese, iron, cobalt, nickel, copper, zinc, gallium, silicon, yttrium, zirconium, niobium, molybdenum, technetium, ruthenium, rhodium, palladium, silver, indium, tin, lanthanum, cerium, praseodymium, neodymium, promethium, samarium, europium, gadolinium, terbium, dysprosium, holmium, erbium, thulium, ytterbium, lutetium, tantalum, tungsten, rhenium, platinum, gold, lead and alloys thereof.

In certain embodiments, the biodegradable metal scaffold is made from an alloy comprising a combination of material that will decompose in the body comparatively rapidly, typically within a period of several months, and form harmless constituents. To obtain uniform corrosion, the alloy may comprises a component, such as magnesium, titanium, zirconium, niobium, tantalum, zinc or silicon, which covers itself with a protective oxide coat. A second component, such as lithium sodium, potassium, calcium, iron or manganese, which possesses sufficient solubility in blood or interstitial fluid, is added to the alloy achieve uniform dissolution of the oxide coat. The corrosion rate can be regulated through the ratio of the two components.

Preferably, the alloy is to be composed so that the corrosion products are soluble salts, such as sodium, potassium, calcium, iron or zinc salts, or that non-soluble corrosion products, such as titanium, tantalum or niobium oxide originate as colloidal particles. The corrosion rate is adjusted by way of the composition so that gases, such as hydrogen which evolves during the corrosion of lithium, sodium, potassium, magnesium, calcium or zinc, dissolve physically, not forming any macroscopic gas bubbles.

The biodegradable metal scaffold may further comprise one or more metal salts. Examples of metal salts include, but are not limited to salts of the following acids: sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid, (glyconic acid, dextronic acid), lactic acid, malic acid, tartaric acid, tartronic acid (hydroxymalonic acid, hydroxypropanedioic acid), fumaric acid, citric acid, ascorbic acid, maleic acid, malonic acid, hydroxymaleic acid, pyruvic acid, phenylacetic acid, (o-, m-, p-) toluic acid, benzoic acid, p-aminobenzoic acid, p-hydroxybenzoic acid, salicylic acid, p-aminosalicylic acid, methanesulfonic acid, ethanesulfonic acid, hydroxyethanesulfonic acid, ethylenesulfonic acid, p-toluenesulfonic acid, naphthylsulfonic acid, naphthylaminesulfonic acid, sulfanilic acid, camphorsulfonic acid, china acid, quinic acid, o-methyl-mandelic acid, hydrogen-benzenesulfonic acid, methionine, tryptophan, lysine, arginine, picric acid (2,4,6-trinitrophenol), adipic acid, d-o-tolyltartaric acid, glutaric acid.

In some embodiments, the metal scaffold comprises a polymer mixed with particles of iron, magnesium, tantalum, zinc, other absorbable metals, or alloys thereof to enhance characteristics of expansion and resistance to compression. In some related embodiments, the particles are nanoparticles.

In some embodiments, the biodegradable metal scaffold is made from a magnesium alloy. In certain embodiments, the magnesium alloy has a magnesium content of at least 20%, 30%, 40%, 50%, 60%, 70%, 80% or 90% (w/w). In other embodiments, the magnesium alloy has a magnesium content of at least 96 wt. %, a manganese content of at least 1 wt. %, and at least one metal from the rare earth metal group in the amount of at least 0.5 wt. %. The rare earth metal group includes lanthanum, cerium, praseodymium, neodymium, promethium, samarium, europium, gadolinium, terbium, dysprosium, holmium, erbium, thulium, ytterbium, lutetium, scandium and yttrium. In another embodiment, the biodegradable metal scaffold is made from a magnesium alloy having a magnesium content of 96-97.9 wt. %, a manganese content of 1.6-2 wt. %, and at least one metal from the rare earth metal group in the amount of 0.5-2 wt. %. In another embodiment, the biodegradable metal scaffold is made from a magnesium alloy having a magnesium content of 97.45 wt. %, a manganese content of 1.8 wt. %, and a cerium content of 0.75 wt. %.

The shape, length and diameter of the in vivo supporting device are application dependent. Each type of the in vivo supporting device is designed to fit within a specific part of the anatomy. Therefore, the shape, length, and diameter of the supporting devices differ by type to accommodate and support different sized lumens and different clinical needs. For example, stent typically has a tubular body. However, each major stent application, such as vascular, pancreatic, ureteral, or metacarpal canal, and other hollow bone structures, requires a different diameter and shape to enable placement, to remain in place after placement, to stabilize and support the anatomy it is placed in, and to allow conformance to the normal anatomy. Most stents bodies define an enclosed or open channel that allows a body fluid to flow though the stents in a body lumen. In certain embodiments, a stent body may further include a center lumen to accommodate a guide wire. This center lumen may provide additionally flow throughput after the removal of guide wire.

The biodegradable metal scaffold can be expandable. In one embodiment, the biodegradable metal scaffold is of two different diametrical dimensions due to radial deformation of its elastic elements. Before being positioned at the place of reconstruction, the biodegradable metal scaffold is deformed/compressed/folded so as to minimize its diametrical dimension. Then the biodegradable metal scaffold is placed, in the deformed state, inside a transporting means by arranging it on a special setting bulb. Once the biodegradable metal scaffold has been transported to the place of reconstruction, the setting bulb is expanded so that the biodegradable metal scaffold diameter is maximized. In another embodiment, the biodegradable metal scaffold has a plurality of flexible or foldable channel walls or leaflets extending from the center rod/hub/cam. The channel walls or leaflets are kept in a folded position during the delivery process and are released only at the treatment site. In other embodiments, the biodegradable metal scaffold is balloon-expandable or is made from a self-expanding metal or alloy, such as nitinol.

In certain embodiments, the biodegradable metal scaffold with thin struts is made from iron or magnesium alloys. In one embodiment, the biodegradable metal scaffold with thin struts is made from a magnesium alloy having a magnesium content of at least 96 wt. %, a manganese content of at least 1 wt. %, and at least one metal from the rare earth metal group in the amount of at least 0.5 wt. %. In another embodiment, the biodegradable metal scaffold is made from a magnesium alloy having a magnesium content of 96-97.9 wt. %, a manganese content of 1.6-2 wt. %, and at least one metal from the rare earth metal group in the amount of 0.5-2 wt. %. In another embodiment, the biodegradable metal scaffold is made from a magnesium alloy having a magnesium content of 97.45 wt. %, a manganese content of 1.8 wt. %, and a cerium content of 0.75 wt. %. Comparing to regular magnesium alloys that do not contain manganese, the manganese-containing magnesium alloys of the present invention have significantly increased mechanical strength and significantly less or slower hydrogen gas production after implantation. In other embodiments, the biodegradable metal scaffold with thin struts is made from magnesium alloys with a high zinc content (e.g., 28 wt % or higher) to reduce hydrogen production after implantation.

In certain embodiments, the biodegradable metal scaffold constitutes less than 50%, 45%, 40%, 35%, 30%, 25% or 20% by weight of the supporting device. In other embodiments, the biodegradable metal scaffold constitutes a minor component of the supporting device. As used herein, the term "minor component" refers to a component of the supporting device that has a smaller weight percentage than another component of the supporting device. For example, the metal scaffold is a minor component in a device having metal content of 40 wt % and a biodegradable polymer content of 45 wt %. In some embodiments, the biodegradable metal scaffold constitutes a minor component of the supporting device and contributes to less than 50% of the overall mechanical strength of the supporting device.

In other embodiments, the supporting device contains magnesium as a minor component of the supporting device. In some embodiments, the supporting device contains magnesium as a minor component at 10-30 wt % of the total device. In some embodiments, the magnesium constitutes a minor component of the supporting device and contributes to less than 50% of the overall mechanical strength of the supporting device.

In certain embodiments, the biodegradable metal scaffold with thin struts needs to be supplemented by the biodegradable polymer coating to achieve sufficient strength to support a vessel. In some embodiments, the biodegradable metal scaffold is expandable after implantation to an expanded form having different diameters at each end of the scaffold. The biodegradable polymer coating helps the scaffold to maintain these diameters after implantation. In other embodiments, the biodegradable metal scaffold is made from an alloy with magnesium as a minor constituent. As used herein, the term "minor constituent" refers to a constituent in an alloy that has a smaller weight percentage than another constituent in the alloy. For example, manganese is a minor constituent in an alloy having a magnesium content of 90 wt. % and a manganese content of 10 wt. %. In some embodiments, the magnesium constitutes a minor constituent of the alloy and the biodegradable metal scaffold contributes to less than 50% of the overall mechanical strength of the supporting device.

In other embodiments, the biodegradable metal scaffold constitutes less than 50% w/w of the in vivo supporting device.

In other embodiments, the biodegradable metal scaffold constitutes less than 50% w/v of the in vivo supporting device.

In other embodiments, the biodegradable metal scaffold constitutes less than 50% v/v of the in vivo supporting device.

In other embodiments, the biodegradable metal scaffold contributes less than 50% of the structure performance of the in vivo supporting device.

In other embodiments, the biodegradable metal scaffold has a magnesium content that is less than 50% w/w of the in vivo supporting device.

In other embodiments, the biodegradable metal scaffold has a magnesium content that is less than 50% w/v of the in vivo supporting device.

In other embodiments, the biodegradable metal scaffold has a magnesium content that is less than 50% v/v of the in vivo supporting device.

In other embodiments, the magnesium in the in vivo supporting device contributes to less than 50% of the structure performance of the in vivo supporting device.

The Biodegradable Polymer Coating or Covering

The biodegradable polymer coating or covering comprises one or more biodegradable polymers. Examples of biodegradable polymers include, but are not limited to, polydioxanone, polycaprolactone, polygluconate, poly(lactic acid) polyethylene oxide copolymer, modified cellulose, polyhydroxybutyrate, polyamino acids, polyphosphate ester, polyvalerolactone, poly-ε-decalactone, polylactonic acid, polyglycolic acid, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerate, poly(1,4-dioxane-2,3-one), poly(1,3-dioxane-2-one), poly-para-dioxanone, polyanhydrides, polymaleic acid anhydrides, polyhydroxy methacrylates, fibrin, poycyanoacrylate, polycaprolactone dimethylacrylates, poly-β-maleic acid, polycaprolactone butyl acrylates, multiblock polymers from oligocaprolactonediols and oligodioxanonediols, polyether ester multiblock polymers from PEG and poly(butylene terephthalates), polypivotolactones, polyglycolic acid trimethyl carbonates, polycaprolactone glycolides, poly(γ-ethyl glutamate), poly(DTH-iminocarbonate), poly(DTE-co-DT-carbonate), poly(bisphenol A-iminocarbonate), polyorthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, carrageenans, fibrinogen, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivates thereof, heparins, chondroitin sulfate, dextran, β-cyclodextrins, copolymers with PEG and polypropylene glycol, gum arabic, guar, gelatin, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, EPDM gums, silicones such as polysiloxanes, polydimethylsiloxanes, polyvinyl halogens and copolymers, cellulose ethers, cellulose triacetates, chitosans and copolymers and/or mixtures of the aforementioned polymers.

In one embodiment, the biodegradable polymer coating or covering comprises a bioabsorable material that is degraded based on varying levels of pH. For example, the material may be stable at a neutral pH but degrades at a high pH. Examples of such materials include, but are not limited to chitin and chitosean. In another embodiment, the bioabsorable material is degradable by enzymes, such as lysozymes. In another embodiment, the biodegradable polymer coating materials bind to the hydrogen atoms in the body fluid and therefore lower the local pH to delay the absorption of the biodegradable polymer coating materials (which are degraded at high pH).

In another embodiment, the biodegradable polymer coating or covering comprises a bioabsorable material that absorbs moisture and expands in situ at the treatment site. For example, a coating made of chitin or a variable copolymer of chitin and PLGA or chitin and magnesium and other raw earth minerals would swell once it comes into contact with various body fluids. In one embodiment, the in vivo supporting device has a pre-implantation diameter $D_{pre}$ (i.e., dry diameter) and is expandable to a post-implantation diameter $D_{post}$, (i.e., wet diameter) after exposure to body liquid in a lumen. As used hereinafter, the "pre-implantation diameter $D_{pre}$" refers to the largest diameter of a device body before implantation and the "post-implantation diameter $D_{post}$" refers to the largest diameter of the device body after implantation.

In certain embodiments, the biodegradable polymer coating or covering is formulated to have a degradable rate that is faster than the degradable rate of the metal scaffold. In other words, the biodegradable polymer coating would dissolve more rapidly than the metal scaffold after implantation. Preferably, the biodegradable polymer coating or covering will cover the entire biodegradable metal scaffold long enough for the device to be fully encapsulated in the tissue so that the metal scaffold is degraded while encapsulated in the tissue, thus avoiding the possibility of releasing metal fragments into a body lumen during degradation. In certain embodiments, the metal scaffold is coated with a biodegradable polymer coating that degrades in one, two, three or four weeks after implantation.

In some other embodiments, the biodegradable polymer coating or covering is mixed with, embedded with, or configured to carry, various agents or cells. Examples of agents that can be mixed with, embedded into or carried by the biodegradable polymer coating include, but are not limited to, small molecule drugs, biologicals and gene transfer vectors.

Examples of small molecule drugs include, but are not limited to, sirolumus, rapamycian, and other antiproliferating agent.

Examples of biologicals include, but are not limited to, antimicrobial agents and chemotherapeutic agents.

The term "antimicrobial agent" as used in the present invention means antibiotics, antiseptics, disinfectants and other synthetic moieties, and combinations thereof, that are soluble in organic solvents such as alcohols, ketones, ethers, aldehydes, acetonitrile, acetic acid, formic acid, methylene chloride and chloroform. Classes of antibiotics that can possibly be used include tetracyclines (i.e., minocycline), rifamycins (i.e., rifampin), macrolides (i.e., erythromycin), penicillins (i.e., nafcillin), cephalosporins (i.e., cefazolin), other β-lactam antibiotics (imipenem, aztreonam), aminoglycosides (i.e., gentamicin), chloramphenicol, sulfonamides (i.e., sulfamethoxazole), glycopeptides (i.e., vancomycm), quinolones (i.e., ciprofloxacin), fusidic acid, trimethoprim, metronidazole, clindamycin, mupirocin, polyenes (i.e., amphotericin B), azoles (i.e., fluconazole) and β-lactam inhibitors (i.e., sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole and nystatin. Other examples of antibiotics, such as those listed in U.S. Pat. No. 4,642,104, herein incorporated by reference, will readily suggest themselves to those of ordinary skill in the art. Examples of antiseptics and disinfectants are thymol, a-terpineol, methylisothiazolone, cetylpyridinium, chloroxylenol, hexachlorophene, cationic biguanides (i.e., chlorhexidine, cyclohexidine), methylenechloride, iodine and iodophores (i.e., povidone-iodine), triclosan, furanmedical preparations (i.e., nitrofurantoin, nitrofurazone), methenamine, aldehydes (i.e., glutaraldehyde, formaldehyde) and alcohols. Other examples of antiseptics and disinfectants will readily suggest themselves to those of ordinary skill in the art.

Chemotherapeutic agents can be mixed with the biodegradable polymer coating in a manner analogous to that of antimicrobial agents. Exemplary chemotherapeutic agents include but are not limited to cis-platinum, paclitaxol, 5-flourouracial, gemcytobine and navelbine. The chemotherapeutic agents are generally grouped as DNA-interactive agents, antimetabolites, tubulin-interactive agents, hormonal agents, hormone-related agents, and others such as asparaginase or hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Don, et al, Cancer Chemotherapy Handbook, 2d edition, pages 15-34, Appleton & Lange (Connecticut, 1994), herein incorporated by reference.

Examples of DNA-interactive agents include, but are not limited to, alkylating agents, DNA strand-breakage agents; intercalating and nonintercalating topoisomerase II inhibitors, and DNA minor groove binders. Alkylating agents generally react with a nucleophilic atom in a cellular constituent, such as an amino, carboxyl, phosphate, or sulfhydryl group in nucleic acids, proteins, amino acids, or glutathione. Examples of alkylating agents include, but are not limited to, nitrogen mustards, such as chlorambucil, cyclophosphamide, isofamide, mechlorethamine, melphalan, uracil mustard; aziridines, such as thiotepa; methanesulfonate esters such as busulfan; nitroso, ureas, such as cannustine, lomustine, streptozocin; platinum complexes, such as cisplatin, carboplatin; bioreductive alkylator, such as mitomycin, and procarbazine, dacarbazine and altretamine. DNA strand breaking agents include, but are not limited to, bleomycin. Intercalating DNA topoisomerase II inhibitors include, but are not limited to, intercalators such as amsacrine, dactinomycin, daunorubicin, doxorubicin, idarubicin, and mitoxantrone.

Nonintercalating DNA topoisomerase II inhibitors include, but are not limited to etoposide and teniposide. DNA minor groove binders include, but are not limited to, plicamycin.

Antimetabolites interfere with the production of nucleic acids by one or the other of two major mechanisms. Some of the drugs inhibit production of the deoxyribonucleoside triphosphates that are immediate precursors for DNA synthesis, thus inhibiting DNA replication. Some of the compounds, for example, purines or pyrimidines, are sufficient to be able to substitute for them in the anabolic nucleotide pathways. These analogs can then be substituted into the DNA and RNA instead of their normal counterparts. The antimetabolites useful herein include: folate antagonists such as methotrexate and trimetrexate pyrimidine antagonists, such as fluorouracil, fluorodeoxyunridine, CB3717, azacytidine, cytarabine, and floxuridine purine antagonists include mercaptopurine, 6-thioguanine, fludarabine, pentostatin; sugar modified analogs include cyctrabine, fludarabine; ribonucleotide reductase inhibitors include hydroxyurea. Tubulin interactive agents act by binding to specific sites on tubulin, a protein that polymerizes to form cellular microtubules. Microtubules are critical cell structure units. When the interactive agents bind on the protein, the cell cannot form microtubules tubulin interactive agents including vincristine and vinblastine, both alkaloids and paclitaxel.

Hormonal agents are also useful in the treatment of cancers and tumors. They are used in hormonally susceptible tumors and are usually derived from natural sources. These include: estrogens, conjugated estrogens and ethinyl estradiol and diethylstilbestrol, chlorotrianisene and idenestrol; progestins such as hydroxyprogesterone caproate, medroxyprogesterone, and megestrol; androgens such as testosterone, testosterone propionate; fluoxymesterone, methyltestosterone; adrenal corticosteroids are derived from natural adrenal cortisol or hydrocortisone. They are used because of their anti-inflammatory benefits as well as the ability of some to inhibit mitotic divisions and to halt DNA synthesis. These compounds include prednisone, dexamethasone, methylprednisolone, and prednisolone.

Hormone-related agents include, but are not limited to, leutinizing hormone releasing hormone agents, gonadotropin-releasing hormone antagonists and anti-hormonal agents. Gonadotropin-releasing hormone antagonists include leuprolide acetate and goserelin acetate. They prevent the biosynthesis of steroids in the testes and are used primarily for the treatment of prostate cancer.

Antihormonal agents include antiestrogenic agents such as tamosifen, antiandrogen agents such as flutamide; and antiadrenal agents such as mitotane and amminoglutethimide. Hydroxyurea appears to act primarily through inhibition of the enzyme ribonucleotide reductase. Asparaginase is an enzyme that converts asparagine to nonfunctional aspartic acid and thus blocks protein synthesis in the tumor.

Gene transfer vectors are capable of introducing a polynucleotide into a cell. The polynucleotide may contain the coding sequence of a protein or a peptide, or a nucleotide sequence that encodes a iRNA or antisense RNA. Examples of gene transfer vectors include, but are not limited to, non-viral vectors and viral vectors. Non-viral vectors typically include a plasmid having a circular double stranded DNA into which additional DNA segments can be introduced. The non-viral vector may be in the form of naked DNA, polycationic condensed DNA linked or unlinked to inactivated virus, ligand linked DNA, and liposome-DNA conjugates. Viral vectors include, but are not limited to, retrovirus, adenovirus, adeno-associated virus (AAV), herpesvirus, and alphavirus vectors. The viral vectors can also be astrovirus, coronavirus, orthomyxovirus, papovavirus, paramyxovirus, parvovirus, picornavirus, poxvirus, or togavirus vectors.

The non-viral and viral vectors also include one or more regulatory sequences operably linked to the polynucleotide being expressed. A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

In one embodiment, the gene transfer vector encodes a short interfering RNA (siRNA). siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing. In another embodiment, the gene transfer vector encodes an antisense RNA.

Examples of cells include, but are not limited to, stem cells or other harvested cells.

In certain embodiments, the biodegradable polymer coating or covering is a multi-layer coating comprising a fast degrading layer and a slow degrading layer. In some embodiments, the fast degrading layer is an outer layer and the slow degrading layer is an inner layer. In some other embodiments, the fast degrading layer is an inner layer and the slow degrading layer is an outer layer.

In some embodiments, the fast degrading layer further comprises an agent that prevents or reduces the post-implantation hyperplastic response. Examples of such an agent include, but are not limited to, paclitaxel and sirolimus. The slow degrading layer may contain the same agent or a different agent, such as the small molecule drugs, biologicals or gene transfer vectors described above. In one embodiment, the fast degrading layer is an inner layer having embedded therein a drug or stem cells. When the slow degrading outer layer is degraded, the fast degrading inner layer quickly releases the drug or cells.

In other embodiments, the fast degrading layer is an outer layer comprising fissures so that body fluid may contact the slow degrading inner layer before the degradation of the outer layer. In the case of an expandable in vivo supporting device, the coating can be made of an elastic polymer composition to allow expansion of the biodegradable metal scaffold while maintaining the integrity of the coating. In another embodiment, the coating a made of a brittle composition that would form fissures when the metal scaffold expands so as to allow simultaneous degradation of both the coating and the metal scaffold. The required elasticity may be achieved using a mixture of crystalline and amorphous polymers, or co-polymers containing both amorphous segments and crystalline segments. For example, poly-D-lactide is amorphous and elastic, while poly-L-lactide has a higher level of crystallinity and is more brittle. A copolymer made of D- and L-lactide would be have an elasticity somewhere in between poly-D-lactide and poly-L-lactide.

In another embodiment, the biodegradable polymer coating or covering is permeable to body fluid to allow simultaneous degradation of both the coating and the metal scaffold after implantation. The permeability of the biodegradable polymer coating or covering may be created by using a porous polymer coating/covering or by creating fissures or holes in the polymer coating/covering during the manufacturing process.

In certain embodiments, the fast degrading outer layer is degradable within 1, 2, 3, 4, 5, 6 or 7 days and the slow degrading inner layer is degradable within 1, 2, 3 and 4 weeks.

The thickness of the outer and inner layers may be adjusted to achieve the desired degradation behavior. In certain embodiments, the thickness of each layer is in the range of 10 μm to 100 μm. In devices with a metal scaffold having very thin struts, the total thickness of the outer and inner coating layers is in the range of 10 μm to 100 In some embodiments, the outer and/or inner coating layer has an uneven thickness.

In some embodiments, the biodegradable polymer coating or covering comprises materials, such as metal particles, that assist with the illumination of the in vivo supporting device under fluoroscopy. Such materials could also be used to help support the material structure of the polymer coating. In some embodiments, the biodegradable polymer coating comprises polymer material mixed with iron or magnesium nanoparticles to help support the polymer material.

In other embodiments, the in vivo supporting device comprises an elastic polymer coating so that it can be used in non-conforming lesions. In some embodiments, the elastic polymer is mixed with metal particles that allow the material to be more malleable to be crimped on the stent and to stay at its dilated from. Examples of such metal particles include, but are not limited to, particles of iron, magnesium, tantalum, zinc and alloys thereof. The metal particles can be of varying sizes and shapes. In certain embodiments, the metal particles are nanoparticles. The coating would have different linked structure and arrangement after crimping or expansion to keep the device compressed or open.

In some embodiment, the biodegradable in vivo supporting devices are closure devices, such as heart failure closure devices for atrial septal defect (ASD), patent foramen *ovale* (PFO) and ventricular septal defect (VSD), fistula closure devices for fistula and closure devices for aneurysm. In some embodiments, the coating or covering is applied via electro spinning or dip coating.

Manufacture of the In Vivo Supporting Device

The biodegradable metal scaffold of the in vivo supporting device can be laser cut, water jet cut, stamped, molded, laythed or formed with other methods commonly used in the art. In one embodiment, the scaffold is cut from a single metal tube. The tube may be hollow or the center may be cored out at varying diameters suitable for the particular indication. The scaffold is then etched and is formed on a suitable shaping device to give the scaffold the desired external geometry. The formed scaffold is then coated with the biodegradable polymer coating using methods well known in the art. In one embodiment, the scaffold is first coated with a slow degrading inner coating and then coated with a fast degrading outer coating.

In certain embodiments, the in vivo supporting device of the present invention are formed in such a way as to allow fluid flow to change in the pitch of the flow to improve flow dynamics and to speed the flow of fluids throughout the device. From a tight radial design to a more longitudinal design.

In one embodiment, spiral surface channels with large cross-section areas are formed to accommodate large volumes of body fluid. In another embodiment, multiple channels with small cross-section area are formed to accommodate large volumes of body fluid. In another embodiment, the device body contains a large center lumen to allow for fluid flow and a plurality of small cross-section area channels on the surface to stabilize the device in vivo.

In another embodiment, the lips of the channel walls are taped to increase the surface area for fluid flow and grip. Changes in the depth of the pitch of the channels will also have an impact on fluid flow and stability.

In one embodiment, the metal scaffold is formed on a shaping tool that has substantially the desired contour of the external stent dimensions. In the event the device is to be shaped to the dimensions of a particular lumen, optical photography and/or optical videography of the target lumen may be conducted prior to stent formation. The geometry of corresponding zones and connector regions of the metal scaffold then can be etched and formed in accordance with the requirements of that target lumen. For example, if the topography of the biliary duct of a particular patient is captured optically and the appropriate dimension provided, a patient specific in vivo supporting device can be engineered. These techniques can be adapted to other non-vascular lumens but is very well suited for vascular applications where patient specific topography is a function of a variety of factors such as genetics, lifestyle, etc.

The in vivo supporting device of the present invention can take on an infinite number of characteristic combinations as zones and segments within a zone can be modified by changing angles, segment lengths, segment thicknesses, pitch during the etching and forming stages of device engineering or during post formation processing and polishing steps. Moreover, by modifying the geometry, depth, and diameter of the channels between zones, additional functionality may be achieved such as flexibility, increased fluid transport, and changes in friction.

The in vivo supporting device of the present invention may be implanted with procedures well known to a person of ordinary skill in the art. Examples of such procedures include, but are not limited to, standard percutaneous approach using a guide wire, endoscopic retrograde cholangiopancreatography (ERCP) placement procedures, and other radiographic/angiographic procedures.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for producing a biodegradable in vivo supporting device, comprising:
  (a) producing a biodegradable metal scaffold made from a magnesium alloy having a magnesium content of 97.45 wt. %, a manganese content of 1.8 wt. %, and a cerium content of 0.75 wt. %;
  (b) coating said biodegradable metal scaffold with a first biodegradable polymer coating having a first degradable rate; and
  (c) coating the biodegradable metal scaffold from step (b) with a second biodegradable polymer coating having a second degradable rate,
  wherein said second degradable rate is faster than said first degradable rate.

2. The method of claim 1, wherein said second biodegradable polymer coating comprises an agent that prevents or reduces the post-implantation hyperplastic response.

3. The method of claim 1, wherein said biodegradable metal scaffold comprises metal struts, wherein said metal struts are covered by said first and second biodegradable polymer coating, wherein said coatings have one or more holes that allow direct contact of the metal strut with a body fluid when said supporting device is placed inside a body lumen.

4. The method of claim 1, wherein said biodegradable metal scaffold comprises metal struts, and wherein said first and second biodegradable polymer coating partially covers said metal struts but does not cover openings between said struts.

5. The method of claim 1, wherein said biodegradable metal scaffold comprises metal struts, and wherein said biodegradable polymer coating covers the exterior surface of said metal struts, including openings between said metal struts.

6. The method of claim 1, further comprising a biodegradable polymer covering that covers the exterior surface of said metal scaffold.

7. The method of claim 6, wherein said covering comprises an agent that prevents or reduces the post-implantation hyperplastic response.

8. The method of claim 1, wherein said biodegradable metal scaffold is a self-expandable scaffold that expands after implantation and wherein said first and second biodegradable polymer coatings are elastic coating that expand with said biodegradable metal scaffold.

9. The method of claim 1, wherein said biodegradable metal scaffold is a self-expandable scaffold that expands after implantation and wherein said first and second biodegradable polymer coatings are coatings that form fissures when said biodegradable metal scaffold expands in vivo.

10. The method of claim 1, wherein said first and second biodegradable polymer coatings are permeable to body fluid.

11. The method of claim 1, wherein said biodegradable metal scaffold constitutes less than 50 wt % of said supporting device.

12. The method of claim 1, wherein said supporting device comprises magnesium as a minor component.

13. The method of claim 1, wherein said biodegradable metal scaffold has a magnesium content that is less than 50 wt % of said supporting device.

14. The method of claim 1, wherein said biodegradable metal scaffold comprises an alloy with magnesium as a minor constituent of said alloy.

15. The method of claim 1, wherein said first biodegradable polymer coating, or said second biodegradable polymer coating, or both comprise a biodegradable polymer and metal particles.

16. The method of claim 15, wherein said metal particles are selected from particles of iron, magnesium, tantalum, zinc and alloys thereof.

* * * * *